(12) United States Patent
Cardy

(10) Patent No.: US 6,566,058 B1
(45) Date of Patent: May 20, 2003

(54) ASSAY INVOLVING LOOPED NUCLEIC ACID

(75) Inventor: Donald L N Cardy, Northamptonshire (GB)

(73) Assignee: British Biocell International Limited, Cardiff (GB)

( * ) Notice: Subject to any disclaimer, the term of this patent is extended or adjusted under 35 U.S.C. 154(b) by 0 days.

(21) Appl. No.: 09/331,053

(22) PCT Filed: Dec. 16, 1997

(86) PCT No.: PCT/GB97/03449

§ 371 (c)(1),
(2), (4) Date: Jun. 16, 1999

(87) PCT Pub. No.: WO98/27225

PCT Pub. Date: Jun. 25, 1998

(30) Foreign Application Priority Data

Dec. 16, 1996 (GB) .............................................. 9626074

(51) Int. Cl.⁷ .......................... C12Q 1/68; C12P 19/34; C07H 21/02; C07H 21/04; C07H 19/00
(52) U.S. Cl. .......................... 435/6; 435/91.1; 435/91.2; 435/91.21; 536/22.1; 536/23.1; 536/24.3; 536/24.31; 536/24.32; 536/24.33
(58) Field of Search .......................... 435/6, 91.1, 91.2, 435/91.21; 536/22.1, 23.1, 24.3, 24.31, 24.32, 24.33

(56) References Cited

U.S. PATENT DOCUMENTS

| | | | | |
|---|---|---|---|---|
| 5,424,413 A | * | 6/1995 | Hogan et al. ............ | 536/24.31 |
| 5,854,033 A | * | 12/1998 | Lizardi ..................... | 435/91.2 |
| 6,183,960 B1 | * | 2/2001 | Lizardi .......................... | 435/6 |

FOREIGN PATENT DOCUMENTS

| | | |
|---|---|---|
| EP | 552 931 | 7/1993 |
| WO | 92/01813 | 2/1992 |
| WO | 93/06240 | 4/1993 |
| WO | 94/03472 | 2/1994 |
| WO | 94/03630 | 2/1994 |
| WO | 97/19193 | 5/1997 |

OTHER PUBLICATIONS

Tyagi S et al: " Molecular Beacons: Probes That Fluoresce Upon Hybridization " Bio/Technology, vol. 14, Mar. 1 1996, pp. 303–308, XP00019602A.

Nilsson M et al: " Padlock Probes: Circularizing Oligonucleotides for Localized DNA Detection " Science, vol. 265, No. 5181, Sep. 30, 1994, pp. 2085–2088, XP000579803.

* cited by examiner

Primary Examiner—Jeffrey Siew
(74) Attorney, Agent, or Firm—Pillsbury Winthrop LLP

(57) ABSTRACT

Disclosed is a method of detecting the presence of a nucleic acid target sequence of interest in a sample, comprising the steps of: (a) reacting the sample containing the target sequence of interest with a first nucleic acid probe, so as to cause hybridization between complementary portions of the target and the probe, wherein the first probe comprises 5' and 3' portions complementary to respective, substantially adjacent portions of the target sequence and an intervening non-complementary portion which does not become hybridized to the target, thereby creating a loop region looped out from a complex formed between the first probe and the target, such that non-contiguous portions of the first probe are brought into close proximity; (b) hybridizing a second nucleic acid probe to the non-contiguous portions of the first probe, (c) initiating nucleic acid synthesis, using the first probe as template, in a manner dependent upon hybridization of the second probe to the first probe; and (d) detecting the newly synthesized nucleic-acid from step (c) above. Also disclosed are kits for performing the method of the invention.

28 Claims, 8 Drawing Sheets

ASSAY INVOLVING LOOPED NUCLEIC ACID

This application is the national phase of international application PCT/GB97/03449 filed Dec. 16, 1997 which designated the U.S.

FIELD OF THE INVENTION

The present invention relates to a method for detecting the presence of a nucleic acid sequence of interest, and to a kit of components for performing the assay method.

BACKGROUND OF THE INVENTION

A number of nucleic acid amplification processes are described in the prior art. One such well known process, polymerase chain reaction (PCR), is disclosed in U.S. Pat. Nos. 4,683,195 and 4,683,202. The PCR process involves the use of nucleic acid primers which anneal to opposite strands of a DNA duplex; these primers are extended using thermostable DNA polymerase in the presence of nucleotide triphosphates to yield two duplex copies of the original nucleic acid sequence. Successive cycles of denaturation, annealing and extension are undertaken in order to further amplify copies of the original nucleic acid sequence.

This method has some disadvantages including the need for adjusting reaction temperatures alternately between intermediate (e.g. 50° C.–55° C.) and high (e.g. 90° C.–95° C.) temperatures, involving repeated thermal cycling. Also the time scale required for multiple cycles of large temperature transitions to achieve amplification of a nucleic acid sequence and the occurrence of sequence errors in the amplified copies of the nucleic acid sequence is a major problem, as errors occur during multiple copying of long sequence tracts. Additionally, detection of the amplified nucleic acid sequence generally requires further processes e.g. agarose gel electrophoresis.

Alternative nucleic acid amplification processes are disclosed in WO 88/10315 (Siska Diagnostics) and European patent nos. 329,822 (Cangene) and 373,960 (Siska Diagnostics). These amplification processes are based on a reaction comprising alternate cycles of DNA and RNA synthesis. This alternating RNA/DNA synthesis is achieved principally through the annealing of oligonucleotides adjacent to a specific DNA sequence, whereby the annealed oligonucleotides comprise a transcriptional promoter and initiation site. The RNA copies of the specific sequence so produced, or alternatively an input sample comprising a specific RNA sequence, are then copied as DNA strands using a nucleic acid primer and the RNA from the resulting DNA:RNA hybrid is either removed by denaturation (WO 88/10315) or removed with RNase H (EP 329,882 and EP 373,960). The annealing of oligonucleotides forming a transcription promoter is then repeated in order to repeat RNA production. Amplification is thus achieved principally through the use of efficient RNA polymerases to produce an excess of RNA copies over DNA templates.

The RNase version of this method has great advantages over PCR in that amplification can potentially be achieved at substantially a single temperature (i.e. isothermally). Additionally, a much greater level of amplification per cycle can be achieved than for PCR i.e. a doubling of DNA copies per cycle for PCR, compared with 10–100 RNA copies per cycle using T7 RNA polymerase. A disadvantage associated with the DNA:RNA cycling method described in EP 329,822 is that it requires test nucleic acid with discrete ends for the annealing of oligonucleotides to create the transcriptional promoter. This poses difficulties in detection of, for example, specific genes in long DNA molecules. Further disadvantages of this method are that at least three enzymes are required to undertake the DNA:RNA cycling with potentially deleterious consequences for stability, cost and reproducibility; and that one or more further processes are invariably required (e.g. gel electrophoresis) for detection of the amplified nucleic acid sequence.

The processes described above all refer to methods whereby a specific nucleic acid region is directly copied and these nucleic acid (RNA and/or DNA) copies are further copied to achieve amplification. The variability between various nucleic acid sequences is such that the rates of amplification between different sequences by the same process are likely to differ thus presenting problems for example in quantitating the original amount of specific nucleic acid.

The prior art methods described above have a number of disadvantages in the amplification of their target nucleic acid. It seems to the present inventors that a method for the sensitive detection of a specific target nucleic acid sequence should have the following characteristics:

a) the process should not necessarily require copying of the target sequence;

b) the process should not involve multiple copying of long tracts of sequence to minimise sequence errors;

c) the process should be generally applicable to both DNA and RNA target sequences, including specific sequences without discrete ends;

d) the signal should result from the two or more different hybridisation events so as to improve specificity;

e) the process should include an option for detection of hybridised probe without any additional processes.

A nucleic acid amplification process that fulfils the above desiderata is disclosed in WO 93/06240 (Cytocell Ltd). This amplification process is centred around the use of two nucleic acid probes which contact the target nucleic acid, portions of said probes being capable of hybridising to the sequence of interest such that the probes are adjacent or substantially adjacent to one another, so as to enable other portions of the first and second probes to become annealed to each other. Following annealing, chain extension of one of the probes is achieved by using part of the other probe as a template. Amplification of the extended probe is typically accomplished by: hybridisation of a further probe substantially complementary to part of the newly synthesised sequence of the extended first probe; extending the further probe by use of an appropriate polymerase using the extended first probe as a template; and separating the extended first and further probes, such that the extended further probe can act as a template for the extension of other first probe molecules, and the extended first probe can act as a template for the extension of other further probe molecules.

Other discolosures of interest include U.S. Pat. Nos. 5,451,503 and 5,424,413 (Gen-Probe, Inc.), which refer to the possibility of forming stem/loop structures upon hybridising a nucleic acid probe to a target sequence. The stem/loop may be formed in either the probe or the target sequence. The documents teach the detection of the duplex stem by various means. WO 97/19193 (Yale University, published May 29, 1997) describes a method of amplifying nucleic acid by means of "rolling circle replication", which produces long concatameric copies of circular probe molecules. The preferred method involves the hybridisation of a linear probe molecule to a target sequence of interest, which brines together non-contiguous portions of the probe molecule, which are then joined in a ligation step to form closed circular nucleic acid molecules. A second probe is hybridised to the circular molecule to initiate rolling circle replication.

Detection of nucleic acid target sequences of interest may be useful clinically (e.g. detecting nucleic acid belonging to pathogens, thus aiding diagnosis of infectious disease, or detecting chromosomal abnormalities such as the "Philadelphia" chromosomal translocation associated with certain cancers), or in public health or environmental fields (e.g. detecting the presence of pathogens such as Salmonella spp in foodstuffs and the like, or detecting *E. coli,* an indicator of faecal contamination, in water supplies and the like).

It should also be mentioned that those skilled in the art are also acquainted with a substance known as PNA (or peptide nucleic acid). PNA comprises the conventional base compounds present in RNA or DNA. However, instead of the bases being covalently bound to a sugar/phosphate backbone, the bases are joined to a peptide backbone. PNA has many properties in common with RNA and DNA: for example, one can form chimeric duplex molecules by annealing a PNA strand to a strand of RNA or DNA. However, PNA also differs from conventional nucleic acid in a number of respects. In particular, the phosphate groups of DNA carry negative charges, and the repulsion between like charges means that hybridisation of DNA strands must generally be performed in the presence of cations (e.g. aqueous salt solutions) to reduce the electrostatic repulsion between the strands. PNA does not comprise negatively charged phosphate groups and so will generally hybridise more readily than conventional nucleic acid strands.

SUMMARY OF THE INVENTION

The present invention typically fulfils all the aforementioned desiderata. In most embodiments, this is achieved by the hybridisation of a long DNA molecule (DNA probe) which 'loops out' non-complementary sequence to the target sequence; a second probe hybridises to the resulting "loop" and may be extended. In the absence of target sequence, no loop is formed therefore the second probe cannot hybridise and hence prime the de novo synthesis of nucleic acid. Moreover, the resulting new complementary nucleic acid can be amplified or detected by a range of alternatives including the use of additional DNA probes or enzymes. An overall scheme for the formation of a loop nucleic acid molecule for subsequent detection or amplification is shown in FIG. 1. It will be understood that either the probe or the target nucleic acid could be looped out in the operation of the present invention.

Therefore, in a first aspect the invention provides a method of detecting the presence of a nucleic acid target sequence of interest in a sample, comprising the steps of:

(a) reacting the sample containing the target sequence of interest with a first nucleic acid probe, so as to cause hybridisation between complementary portions of the target and the probe, wherein the probe comprises 5' and 3' portions complementary to respective, substantially adjacent portions of the target sequence and an intervening non-complementary portion which does not become hybridised to the target, thereby creating a loop region looped out from a complex formed between the first probe and the target, such that non-contiguous portions of the first probe are brought into close proximity;

(b) hybridising a second nucleic acid probe to the non-contiguous portions of the first probe;

(c) initiating nucleic acid synthesis, using the first probe as template, in a manner dependent upon hybridisation of the second probe to the first probe; and (d) detecting the newly synthesized nucleic acid from step (c) above.

The method of the invention may be used qualitatively or quantitatively.

Those skilled in the art will appreciate that the first and/or second nucleic acid probes need not consist exclusively of nucleic acid but may comprise e.g. PNA, or labelling reagents. Similarly, the target may comprise RNA or DNA.

Generally the first probe will comprise between 50 and 5,000 nucleotides, preferably between 75 and 1,000 nucleotides. The 5' and 3' portions complementary to the target sequence may be of different length (in one embodiment, detailed below, the 5' complementary portion is much longer than the 3' complementary portion). Typically each complementary portion will comprise between 16 and 35 nucleotides. The intervening non-complementary portion of the first probe will typically comprise 30–1,000 nucleotides, preferably 50–500 nucleotides.

The second probe will normally be smaller than the first probe, typically comprising 15–100 nucleotides, preferably 15–50 nucleotides.

Those skilled in the art will appreciate that the second probe will hybridise to the intervening portion of the first probe only if the 5' and 3' complementary portions of the first probe are themselves hybridised to the target sequence of interest: it is the hybridisation of the 5' and 3' complementary portions to the target which brings into close proximity the non-contiguous parts of the intervening portion of the first probe which, in the absence of the target sequence of interest, remain separated from each other. Accordingly, the 5' and 3' portions of the first probe must hybridise to respective complementary portions of the target which are substantially adjacent (e.g. within 10 nucleotides, preferably within 5 nucleotides of each other, most preferably contiguous).

The second nucleotide probe is preferably designed such that each region of complementarity to the juxtaposed non-contiguous loop sequences has a melting temperature [Tm] of at least Tm −10° C. of the total Tm for the annealing of the whole molecule. Therefore, the assay conditions are preferably designed such that annealing of probes occurs at greater than Tm +10° C. (preferably +15° C.) above the Tm of the separate complementary regions of the second probe. Hence, hybridisation of the second probe will only occur when sequences in the loop become juxtaposed i.e. only in the presence of target under the assay conditions.

The precise conditions selected for performance of the assay will depend on the length and sequence of the probes and the target. The person skilled in the art will readily be able to vary the conditions if necessary, using trial and error, to obtain appropriate results, with the benefit of the present disclosure.

Once the first and second probes have hybridised to each other, two alternative methods are envisaged for initiating nucleic acid synthesis according to step (c) above.

In one method (the "primer extension" method), the second probe acts as a primer for de novo nucleic acid synthesis using the first probe as a template. Nucleotides are added to the 3' end of the second probe in a conventional manner by an RNA or DNA polymerase. Preferably a DNA polymerase is used, to synthesis DNA (although, mutant forms of RNA are known which may synthesise RNA or DNA [see: Kostyuk et al., 1995 FEBS Letts. 369, 165–168]). If desired, the newly synthesised nucleic acid may incorporate labelling reagents (e.g. nucleotides or nucleotide analogues labelled with fluorescent tags, or radiolabels) to facilitate detection of the newly synthesised nucleic acid (in step (d) above).

In embodiments using the "primer extension" method, it is preferred that the 3' end of the first probe is blocked, to prevent the first probe being extended in competition with extension of the second probe. Suitable blocking means are well known to those skilled in the art and include, for example, the use of phosphate groups or of nucleotide analogues (e.g. a dideoxynucleotide) at the 3' end, which prevent extension by polvmerase enzymes.

The nature of the primer extension reaction will largely be determined by the choice of polvmerase. Thus, for example, if a highly prodessive polymerase is employed, one may obtain rolling circle replication of the first probe. Polyinerases suitable for rolling circle replication ideally are capable of displacing the second probe from the first probe template (i.e. have a "strand displacement" activity), which is necessary to obtain multiple copies of the first probe. It is also preferred that such polymerases lack a 5' to 3' exonuclease activity which, if present, would tend to cause digestion of the newly-synthesised nucleic acid. In some embodiments of the present invention the template (i.e. the first probe) is not a covalently closed circular nucleic acid molecule (e.g. is a loop, in which the ends are very close together). Accordingly, it is preferred that a highly processive enzyme is employed in such embodiments if rolling circule replication is desired. A particularly preferred polymerase is that obtainable from phage ø29 (see U.S. Pat. Nos. 5,198,543 and 5,001,050 and Gutiérrez et al, 1991 J. Biol. Chem. 266, 2104–2111). Less preferred are polymerases obtainable from phage M2 (see Matsumoto et al, 1989 Gene 84, 247) or that obtainable from phage øPRD1 (see Jung et al, 1987 Proc. Natl. Acad. Sci. USA 84, 8287) or polymerases from M13 or øx 174. In other embodiments, described below, the first probe can be made into a covalently closed molecule and less processive enzymes may be employed and rolling circle replication may still result. Other polymerases which may be suitable are disclosed in WO 97/19193.

It is noted that strand displacement factors (e.g. helicases) may be of assistance in obtaining rolling circle replication, and that such factors may allow an enzyme to perform rolling circle replication which would not normally be caused by such an enzyme in the absence of a strand displacement factor. A number of strand displacement factors are known to those skilled in the art (e.g. calf thymes helicase, disclosed by Siegal et al, 1992 J. Biol. Chem. 267, 13,629). Other strand displacement factors are described in WO 97/19193.

As outlined above, in some embodiments, the first probe can be converted into a covalently closed molecule, which facilitates the performance of rolling cirle replication. In such embodiments the first probe comprises, internal to the 5' and 3' portions complementary to the target, two relatively short self-complementary regions, one (the "5' self-complementary sequence") substantially internally adjacent to the target-complementary 5' portion, and one (the "3' self-complementary sequence") substantially internally adjacent to the target-complementary 3' portion, such that the self-complementary portions flank the intervening non-complementary portion.

When the 5' and 3' target-complementary portions hybridise to the target, they bring into close proximity the 5' and 3' self-complementary sequences, allowing them to anneal to each other forming a stem structure supporting the looped out non-complementary intervening portion. Each self-complementary sequence typically comprises between 4 and 20 nucleotides, preferably between 6 and 12 nucleotides, such that the stem structure (when formed) comprises a corresponding number of base pairs. Those skilled in the art will appreciate that the self-complementary sequences must be short relative to the 5' and 3' target-complementary portions, otherwise the self-complementary sequences may become annealed in the absence of the target sequence, which would in turn allow the second probe to hybridise to the first probe. Accordingly, the region of complementarity producing the stem will preferably be such that the Tm of the stem structure will be less than the overall Tm of the structure stabilised by target nucleic acid. Hence, assay conditions are designed such that the reaction proceeds at least +10° C. (preferably +15° C.) above the Tm of the stem complementary region.

The double stranded stem structure formed by the annealing of the 5' and 3' self-complementary sequences will typically comprise a cleavage site, preferably a restriction endonuclease recognition site. The sequence of the first and second probes will preferably be designed such that the site will be unique to the stem structure. Whilst a restriction endonuclease site is preferred, other specific cleavage sites may be employed (e.g. one recognised by a ribozyme, or by a cleavase). Alternatively, moderately specific cleavage may be obtained by chemical treatment (e.g. with EDTA or other $Fe^{2+}$ chelator).

Accordingly, treatment of the complex formed between the target, the first probe and the second probe, with the appropriate cleavage mediator (e.g. restriction endonuclease) will cleave the stem structure, releasing the first probe (and any second probe hybridised thereto) from the target sequence. Cleavage of the probe(s) from the target sequence may have the advantage of facilitating subsequent nucleic acid synthesis and/or detection of newly synthesised nucleic acid (e.g. by avoiding steric hindrance resulting from the presence of a possibly very large target sequence). The second probe is desirably selected so as to comprise a short sequence which is complementary to the 5' and 3' self-complementary sequences. Accordingly, the second probe is able to hybridise fully to the self-complementary sequences of the first probe once the stem structure has been cleaved by the endonuclease. Thus, a molecule is formed which comprises partially double stranded, nicked nucleic acid. As will be apparent to those skilled in the art, such a structure may be covalently closed by a ligase, yielding covalently closed circular first probe molecule to which is hybridised the second probe. Primer extension (or, more particularly, rolling circle replication) may then proceed as is conventionally known.

In general, once the second probe molecule has been extended, the newly synthesised nucleic acid may be detected by any of a number of techniques already known to those skilled in the art. As described above, the newly synthesised nucleic acid may incorporate labelling reagents. Alternatively, the nucleic acid may be detected and identified by electrophoresis on polyacrylamide or agarose gels (including the use of capillary electrophoresis, as described by Schwartz & Ulfelder [1992 Anal. Chem. 64, 1737]; or by the hybridisation of a complementary labelled nucleic acid probe; or by the binding of some other sequence-specific reagent (e.g. antibody or antibody fragment, or DNA-binding protein, such as a zinc-finger protein. and the like), such as performance of enzyme linked oligonucleotide sorbant assay (ELOSA), described by Berg er al, (1996 Molec. Cellular Probes 10, 7–14); or by fluorescence polarisation (e.g. see "Detection of Amplified DNA by Fluorescence polarization" [1995] in Beacon Fluorescence Polarization System—Applications Guide, PanVera Corporation, Madison, USA).

A particularly preferred detection method is the use of a "molecule beacon", which technique is described by Tyagi & Kramer (1996 Nature Biotechnology 14, 303). In essence, the technique involves the provision of a molecular beacon sequence which is complementary to the sequence to be detected (i.e. the newly synthesised nucleic acid). The molecular beacon comprises at one end a fluorophore, and at the other end a quenching moiety. The molecular beacon also comprises short self-complemertary sequences which, in the absence of the nucleic acid to be detected, remain annealed such that the quenching moiety is in close proximity to the fluorophore and quenches any fluorescence generated by the fluorophore. However, in the presence of a complementary sequence to be detected the molecular beacon is opened out, separating the fluorophore from the quenching moiety and allowing the fluorophore to fluoresce uninhibited. which fluorescence may be detected in the conventional manner. Suitable fluorophores include FAM (FAM is an abbreviation for "fluorescein addition monomers", which refers to 6 carboxy-fluorescein), EDANS (5-[2'-aminoethyl]aminonaphthalene-1-sulfonic acid), and DABCYL (4-[4'-dimethylaminophenylazo]benzoic acid), and a suitable quenching moiety for FAM includes methyl red.

In a preferred embodiment primer extension of the second probe (whether by rolling circle replication or by conventional "linear" primer extension) results in the formation of a functional, double-stranded RNA promoter. Thus, the first probe will comprise one strand of an RNA promoter sequence, and the second strand is provided by extension of the second probe. Numerous suitable RNA promoter sequences are known. Accordingly, upon the formation of such an RNA promoter sequence, the corresponding RNA polymerase will synthesise RNA copies of the first probe in the presence of a supply of ribonucleotides. The two preferred RNA polymerases are T7 RNA polymerase and SP6 RNA polymerase, which are both commercially available and have been well characterised. Other RNA polymerases. with known promoter sequences, may also be suitable. An advantage of this embodiment is that the RNA copies may be produced isothermally (i.e. no temperature cycling is required in order to obtain amplification).

It is preferred that extension of the second probe results in the formation of a plurality of RNA promoters. This may be achieved by designing the sequence of the first probe to comprise a plurality of single stranded RNA promoter sequences, such that synthesis of the complementary nucleic acid strand (by extension of the second probe) results in the formation of a plurality of active, double stranded RNA promoters. This has the advantage of allowing for the production of multiple RNA sequences in a single cycle of RNA synthesis, giving increased amplification of the "signal" generated by the presence of a single target sequence of interest.

The RNA copies of the first probe may be detected by ally of the known methods outlined previously (e.g. gel electrophoresis, hybridisation to complementary labelled sequences, incorporation of labelled ribonucleotides, etc). Alternatively, the sequence of the first probe may be such that the RNA copies thereof may act as messenger RNA molecules which, upon translation, produce a detectable polypeptide. A particularly suitable polypeptide would be a small activator molecule, which activates an enzyme or enzyme precursor. An example of such an activator molecule is the α peptide of β-galactosidase, which activates the M15 mutant form of β-galactosidase. The activated enzyme can be used to give an easily readable colourimetric assay, in the presence of a suitable substrate. This type of assay is described in greater detail in WO 93/01313.

In a particular embodiment, rolling circle replication of the first probe is performed by a DNA polymerase, producing a long, concatameric nucleic acid molecule which comprises a plurality of tandem repeats of the sequence complementary to the first probe sequence. Each repeat may comprise one or more single stranded RNA promoters. If the first probe molecule is present in excess (or additional first probe is added after the initial hybridisation to the target sequence) it will hybridise to the newly synthesised complementary strand, thus forming active double stranded RNA promoters, which can be used to produce multiple RNA molecules for detection as described previously.

In some embodiments, the second probe: comprises a short 5' portion which is not complementary to the first probe, and thus produces a 5' tail. This has the advantage of facilitating strand displacement, and so assists in extension of the second probe past its original 5' end. Thus, (using a polymerase without a significant 5' to 3' exonuclease activity), there is enhanced likelihood of obtaining rolling circle replication. Alternatively, in other embodiments, displacement of the 5' end of the original second probe allows extension of nucleic acid synthesis along towards the 5' end of the first probe, rather than repeated rolling circle replication within the looped out region of the first probe. One may envisage embodiments where, if the 5' target-complementary portion of the first probe is sufficiently long, and the 3' target-complementary portion of the first probe is sufficiently short, strand displacement of the 5' target-complementary portion during extension of the second probe may be sufficient to destabilise entirely the hybridization between the target sequence and the first probe, such that first probe molecule becomes removed from the target sequence. If fresh first probe molecules are available (e.g. by addition of extra molecules, or because of presence in excess ab initio), they may then become hybridised to the target sequence, annealed to by a second probe molecule, and the cycle repeated by extension of the second probe, and so on. This embodiment may be favoured if there are self-complementary portions in the first probe which form a stem, as described previously.

The foregoing generally relates to embodiments of the invention in which the second probe is subjected to primer extension. However, in an other embodiments, an active RNA promoter is formed simply by the hybridisation of the second probe to the first probe. RNA copies of the first probe may then be synthesised and detected as described above.

It will be apparent to those skilled in the art that a substantially equivalent topological arrangement may be obtained by hybridising a probe so as to cause looping out of the target sequence. Such a method is normally less preferable, because if the target sequence is to be looped out one has less flexibility in selection of the sequence of the looped out region, whereas if the first probe is looped out, one can select and design the sequence of the probe for desirable characteristics to a much greater degree.

Thus, in a second aspect the invention provides a method for detecting the presence of a nucleic acid target sequence of interest in a sample, comprising the steps of:

(a) reacting the sample containing the target sequence of interest with a first nucleic acid probe, so as to cause hybridisation between complementary portions of the target and the probe, wherein the target comprises 5' and 3' portions complementary to respective, substantially adjacent portions of the probe and an intervening non-complementary portion which does not become hybridised to the probe, thereby creating a loop region looped out from a complex formed between the probe and the target, such that non-contiguous portions of the target are brought into close proximity;

(b) hybridising a second nucleic acid probe to the non-contiguous portions of the target;

(c) initiating nucleic acid synthesis using the target as template, in a manner dependent upon hybridisation of the second probe to the target; and (d) detecting the newly synthesised nucleic acid from step (c) above.

Those skilled in the art will appreciate that the techniques used to perform the method of the first aspect of the invention will be broadly applicable to the method of the second aspect, defined above. It may be possible to select a portion of the target sequence which comprises a single stranded RNA promoter, which will be complemented by hybridisation and/or extension of the second probe to form an active double stranded promoter. Alternatively primer extension of the second probe may result in the incorporation of labelled nucleotides or nucleotide analogues (e.g. by rolling circle replication).

In a third aspect the invention provides a kit for performing the method of the first aspect, the kit comprising a first nucleic acid probe molecule for hybridisation to the target sequence of interest, a second nucleic acid probe molecule for hybridisation to non-contiguous portions of the first probe molecule which are brought into close proximity upon hybridisation of the first probe to the target, and instructions for use according to the first aspect. The kit will typically further comprise a DNA polyrnerase and/or an RNA polymerase. Further optional components of the kit include: nucleotides (ribonucleotides or deoxyribonucleotides) for synthesis of nucleic acid; detection reagents (e.g. labelling reagents such as labelled nucleotides or nucleotide analogues, molecular beacon sequences); enzyme cofactors; strand displacement factors; reaction buffers (e.g. for performing hybridisation, or nucleic acid synthesis) and the like. The different components of the kit will typically be provided as an aliquot or aliquots within a package.

The invention will now be further described by way of illustrative example and with reference to the accompanying drawings, in which:

EXAMPLE 1

Figure 1:
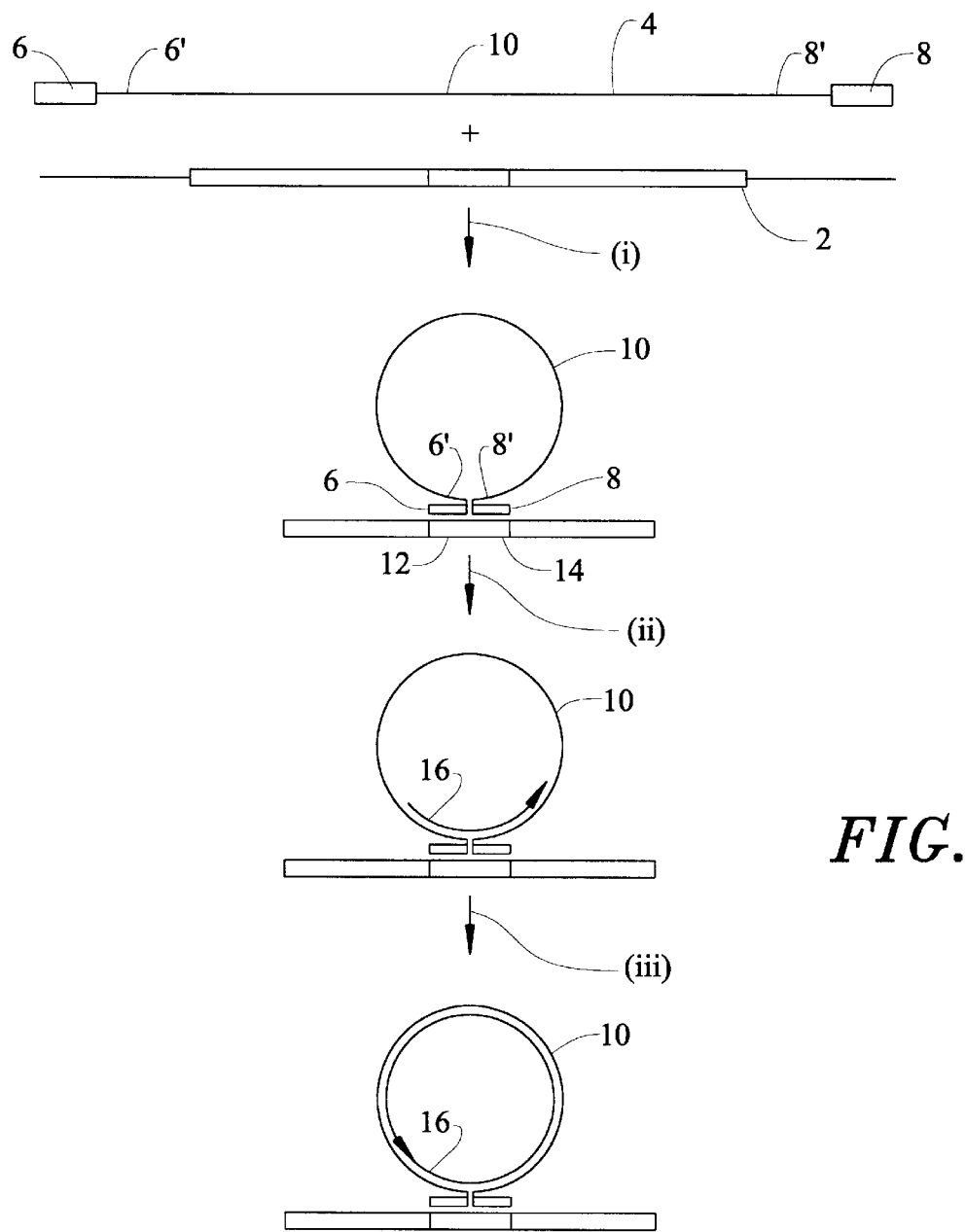
FIG. 1 is a schematic representation of the principle features of the method of the first aspect of the invention.

The general principle of the method of the first aspect of the invention is illustrated schematically in FIG. 1.

Referring to FIG. 1, a target sequence 2 is reacted with a first nucleic acid probe 4 under suitable hybridisation conditions. The probe 4 comprises a 5' target-complementary portion 6, and 3' target-complementary portion 8. and an intervening portion 10 which is not complementary to the target sequence 2. The 5' and 3' target-complementary portions (6, 8) are complementary to respective substantially adjacent portions (12, 14) of the target sequence 2, such that upon hybridisation of the probe 4 to the target sequence 2, non-contiguous portions 6' and 8' of the probe 4 are brought into close proximity (step (i)), whilst the rest of the intervening portion 10 is looped out. In step (ii) a second nucleic acid probe 16 is hybridised to the non-contiguous portions 6', 8' of the probe 4, in such a manner that nucleic acid synthesis may occur, using the first probe 4 as template (indicated in step (iii) as extension of the second probe 16). Variants of this general principle have been described above.

EXAMPLE 2

This example demonstrates the use of the method of the first aspect of the invention for the detection of target nucleic acid (the Hepatitis B surface antigen gene), as a result of interaction with first and second probes to yield a de novo primer extended nucleic acid concatamer product. The example is illustrated schematically in FIG. 2.

2.1. Preparation of Oligonucleotides

The target nucleic acid and first and second probes are synthesised by phosphoramidite chemistry using an Applied Biosystems 380A synthesiser, according to the manufacturer's instructions. All oligonucleotides are HPLC purified using standard techniques.

2.2. Looping Out of Probe Amplification

Hybridisation reactions comprise mixtures of DNA including target DNA (Hepatitis B surface antigen gene sequence), first and second probes, together with controls comprising mixtures with and without target or first and second probes. For hybridisation reactions, 100 ng of target Hepatitis B oligonucleotide is mixed with 100 ng first probe and 100 ng second probe in a solution containing 0.2 mM dNTP mix, 2.5 µl 10× φ29 buffer, and distilled water to 25 µl. The mixture is heated to 94° C. for 0.5 minutes to denature the nucleic acids, primers annealed at 47° C. and extended at 37° C. for 90 minutes by addition of 5 units φ29 polymerase. An aliquot (5µl) of the resulting product is fractionated by electrophoresis through a 1.5% Metaphor (FMC) agarose gel to observe and identify the primer extended product.

2.3. Oligonucleotides

Target Sequence

5' TTTCTCCTGGCTCAGTTTACTAGTGCCATTT GTTCAGTGGTTCGCAGGGCTTTCCCCCACTGT TTGGCTTT 3' (Seq. ID No. 1)

First Probe

5' GGGAAAGCCCTGCGAACCACTCGTGGAATG TTGCCCACACCTAGTGCCCACCGTGGAATGT TGCCCACACCTAGTGCCCACGAACAAATGGC ACTAGTAAACp 3' (Seq. ID No. 2)

Second Probe

5' CCACGGTGGGCACTA 3' (Seq. ID No. 3)

Figure 2:
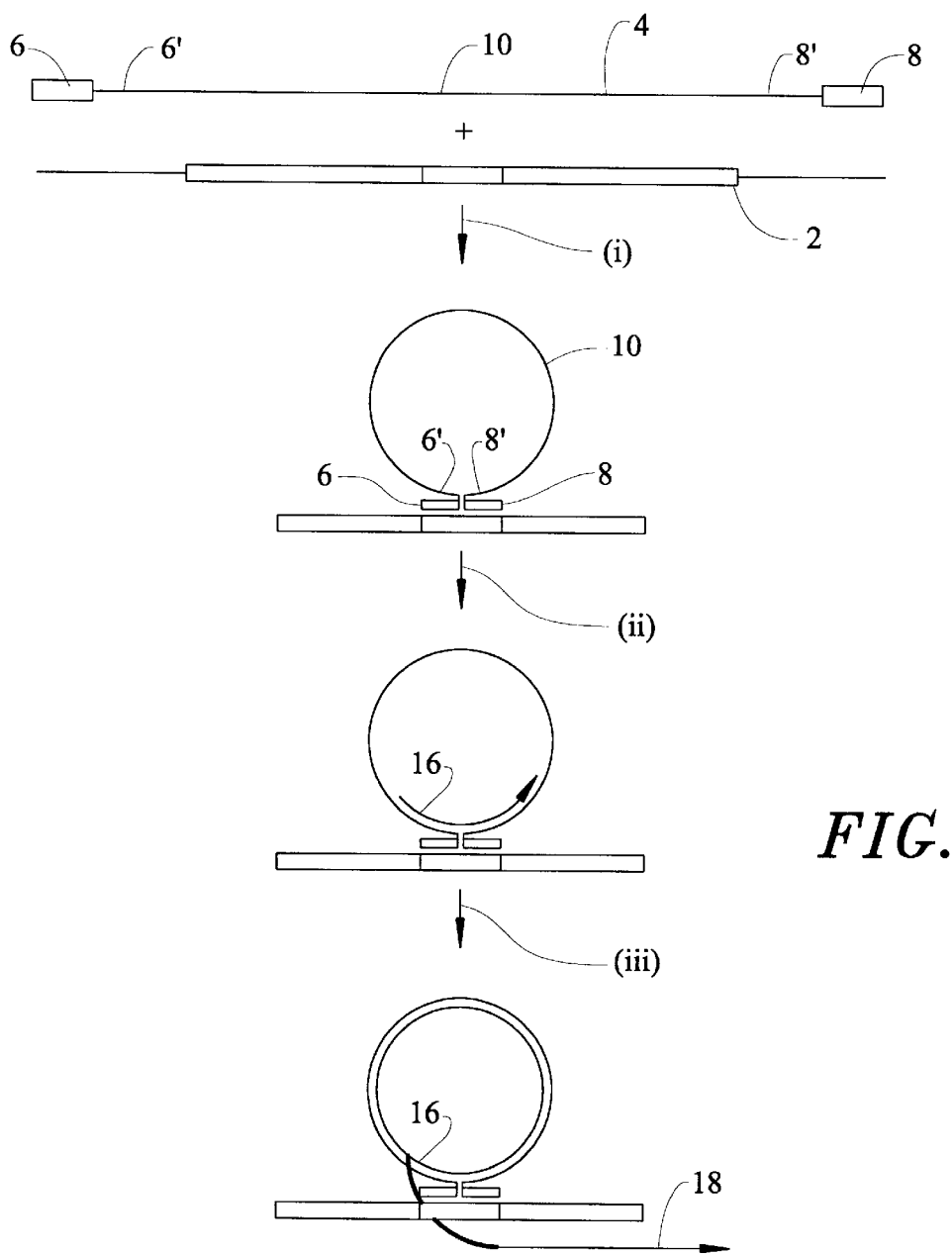
FIGS. 2–5 and 7–8 are schematic representations of particular embodiments of the invention.

Equivalent components in FIG. 2 are denoted with the same reference numerals as used in FIG. 1. Referring to FIG. 2, steps (i) and (ii) are performed essentially as described in Example 1. In step (iii), second probe 16 is extended by use of the highly processive DNA polymerase from phage ø29, resulting in rolling circle replication, producing a long concatameric molecule of newly synthesised nucleic acid 18 which can be detected by a number of means, including agarose gel electrophoresis (with visualisation in UV light, for example, in the presence of an intercalating dye).

EXAMPLE 3

This example demonstrates the formation of a functional T7 DNA dependent RNA polymerase promoter as a result of the interaction of target nucleic acid (the carA gene from *N. gonorrhoeae*) and hybridised probes, to yield a de novo synthesised RNA in the presence of T7 RNA polymerase. The method is illustrated schematically in FIG. 3.

3.1. Preparation of Oligonucleotides

The target oligonucleotide and first and second probes are synthesised by phosphoramidite chemistry using an Applied Biosystems 380A synthesiser, according to the manufacturer's instructions. All oligonucleotides are HPLC purified using standard techniques.

3.2. Looping Out of Probe and RNA Synthesis

Hybridisation reactions comprise mixtures of DNA including target oligonucleotide, first and second probes together with relevant controls comprising mixtures with and without target or first and second probes. For hybridisation reactions, 100 ng of target oligonucleotide was mixed with 100 ng of first probe and 200 ng of second probe in a solution containing 40 nmoles rNTP mix, 4 µl 5× T7 RNA polymerase buffer, and distilled water to 20 µl. The mixture is heated to 90° C. for 3 minutes to denature the inucleic acids, incubated on ice for 2 minutes, and primers annealed and transcribed at 37° C. for 180 minutes by addition of 40 units T7 RNA polymerase. The resulting product is detected by the hybridisation of molecular beacon, as described below.

3.3. Detection of RNA by Molecular Beacon Assay

5 µl of reaction sample is added to the reaction mix consisting of 145 µl hybridisation solution and 2 picomol molecular beacon (fluorochrome=FAM; quencher=methyl red), in a Labsystems Whitestrip well plate, which is incubated in the dark with shaking at 22° C. for 1 hour. Fluorescence signal from the hybridised beacon/target is measured using the Wallac Victor 1420 Multilabel Counter, using the fluorescein protocol.

Figure 3:
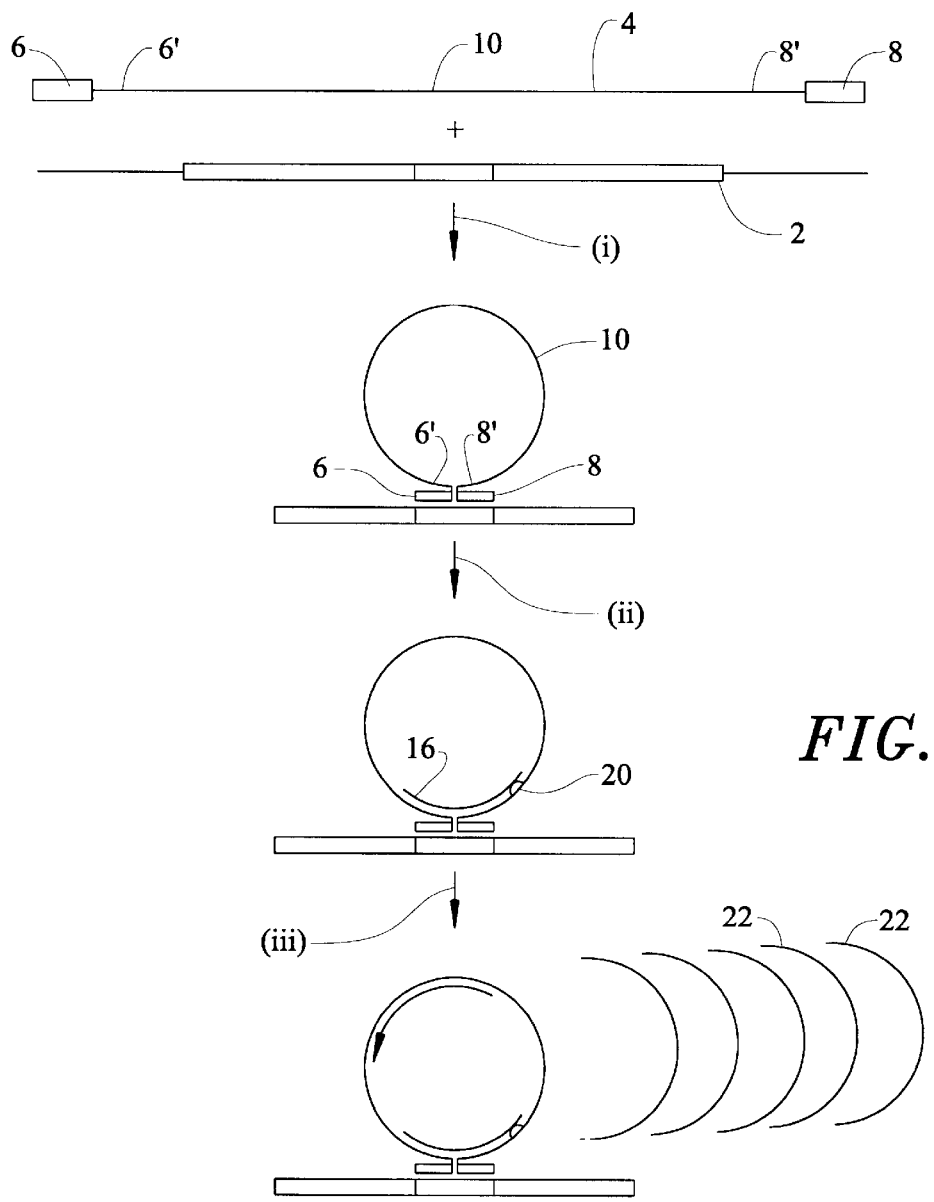

FIG. 3 is a schematic representation of the example detailed above. Functionally equivalent integers are denoted using the same reference numerals as in FIGS. 1 and 2.

Referring to FIG. 3, steps (i) and (ii) are performed essentially as described in Example 1. However, first probe 4 comprises a sequence which constitutes an inactive single stranded RNA promoter. Upon hybridisation of the complementary portion of the second probe 16, an active double stranded T7 RNA polymerase promoter 20 is formed.

Addition of T7 RNA polymerase (step (iii)) leads to transcription from the RNA promoter site, producing multiple RNA copies 22 of the first probe 4 which may be detected by any one of a number of means. In this example they are detected by hybridisation to a fluorescent molecular beacon oligonucleotide.

EXAMPLE 4

This example demonstrates the formation of a functional T7 DNA dependent RNA polymerase promoter as a result of the interaction of target nucleic acid (the E6 oncogene from HPV 16) and hybridised probes. Primer extension of one of these probes produces the functional promoter and enables the de novo synthesis of RNA in the presence of T7 RNA polymerase. The example is represented schematically in FIG. 4.

4.1. Preparation of Oligonucleotides

The target oligonucleotide and first and second probes are synthesised by phosphoramidite chemistry using an Applied Biosystems 380A synthesiser, according to the manufacturer's instructions. All oligonucleotides are HPLC purified using standard techniques.

4.2. Looping Out of Probe, Primer Extension and RNA Synthesis

Hybridisation reactions comprise mixtures of DNA including target oligonucleotide, first and second probes together with relevant controls comprising mixtures with and without target or first and second probes. For hybridisation reactions, 100 ng of target oligonucleotide is mixed with 100 ng of first probe and 200 ng of second probe in a solution containing 10 nmoles dNTP, 40 nmoles rNTP mix, 4 µl 5×reaction buffer, and molecular biology grade water to 20 µl. The mixture is heated to 90° C. for 3 minutes to denature the nucleic acids, incubated on ice for 2 minutes, and primers annealed at 49° C., extended and RNA transcribed at 37° C. for 180 minutes by addition of 2.5 units of Klenow (exo⁻) DNA polymerase and 40 units T7 RNA polymerase. The resulting product is detected by the hybridisation of molecular beacon as described in Example 3.

4.3. Oligonucleotides

Target Sequence
   5' CATCGACCGGTCCACCGACCCCTTATATTA TGGAATCTTTGCTTTTTGTCCAGATGTCTTT GCTTTTCTTCAGGACACAGTGGCTTTTGACAG TTAATAC 3' (Seq. ID No. 4)

First Probe
   5' AAAGCCACTGTGTCCTGAAGGTATTAATTT CCGTGGAATGTTGCCCACACCTAGTGCCCA CCGTGGAATGTTGCCCACACCTAGTGCCCA CCGTGGAATGTTGCCCACACCTAGTGCCCAC TCTCCCTATAGTGAGTCAAAAGCAAAGACA TCTGGAp 3' (Seq. ID No. 5)

Second Probe
   5' CCACGGAAATTAATACGACT 3' (Seq. ID No. 6)

Molecular Beacon Oligonucleotide
   5' CGCGCGTGGAATGTTGCCCACACCTAGTGCC CACCGCG 3' (Seq. ID No. 7)

Figure 4:
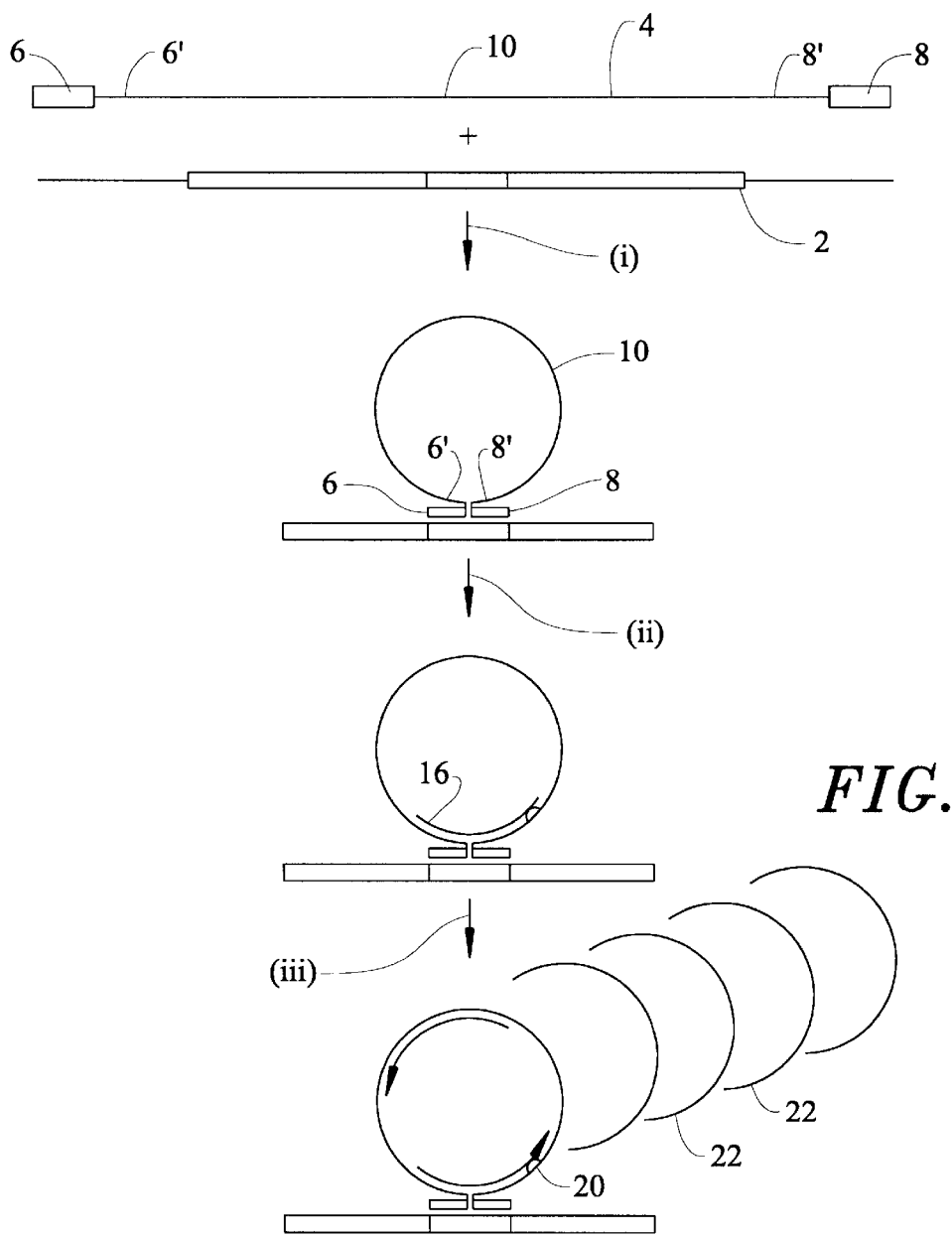

The example is represented schematically in FIG. 4. Functionally equivalent integers are denoted by the same reference numerals used in FIGS. 1 and 2.

Referring to FIG. 4, steps (i) and (ii) are performed essentially as described in Example 1. However, unlike in Example 3, mere hybridisation of the second probe 16 to the first probe 4 is insufficient to generate an active RNA promoter. The RNA promoter sequence is located more 5' on the first probe 4 than in Example 3, such that primer extension of the second probe 16, using Klenow polymerase (or other exonuclease deficient polymerase), is necessary to produce nucleic acid complementary to the RNA promoter sequence on the first probe 4. Once the second probe 16 is extended however, an active RNA promoter 20 is formed which, upon addition of the T7 RNA polymerase (in step (iii)), produces multiple RNA copies 22 of the first probe 4.

EXAMPLE 5

This example demonstrates the synthesis of a de novo nucleic acid concatamer as a result of the interaction of target nucleic acid (a specific sequence from Human cytomegalovirus), and hybridised probes, followed by specific restriction, release and ligation of a closed circular nucleic acid. The closed circular nucleic acid subsequently acts as a template for the synthesis of a de novo primer extended product following the annealing of an extension primer. The example is illustrated schematically in FIG. 5.

5.1. Preparation of Oligonucleotides

The target nucleic acid and first and second probes are synthesised by phosphoramidite chemistry using an Applied Biosystems 380A synthesiser, according to the manufacturers instructions. All oligonucleotides are HPLC purified using standard techniques.

5.2. Looping Out of Probe, Circularisation and Amplification

Hybridisation reactions comprise mixtures of DNA including target DNA (Human cytomegalovirus sequence), and first and second probes together with controls comprising mixtures with and without target or first and second probes. For hybridisation reactions, 100 ng of target oligonucleotide is mixed with 100 ng of first probe and 100 ng of second probe in a solution containing 0.2 mM dNTP mix, 4 µl 5×universal buffer, and distilled water to 20 µl. The mixture is heated to 94° C. for 0.5 minutes to denature the nucleic acids, primers annealed at 50° C. for 10 minutes, followed by 30 minute incubation at 37° C. in the presence of 5 units Stu1 restriction endonuclease. Following restriction, 5 units of T4 DNA ligase and 10 units φ29 polymerase is added and incubated at 37° C. for 90 minutes. Detection of the resulting primer extended product is achieved through the hybridisation of a molecular beacon (as described previously).

5.3. Olionucleotides

Target Sequence

5' GCGTCGTTTCCGCGTCGCTGGCCCCTGGGA GGCGTTCTTCGTGTGTCCCCGGGGACCCGC GCTGCCGTCG 3' (Seq. ID No. 8)

First Probe

5' CCCCGGGGACACACGAAGAAAGGCCTCCCAC CTTTCGAGGCCGCCACGTCCTACCCACCTT TCGAGGCCGCCACGTCCTACCCACCTTTCGAG GCC GCCACGTCCTTGAAGGCCTCGCCTCCCAG GGGCCAGCGAp 3' (Seq. ID No. 9) (underlined portion denotes StuI site of stem region)

Second Probe

5' GGTGGGAGGCCTTCAAGGACGTGG 3' (Seq. ID No. 10)

Molecular Beacon Oligonucleotide

5'CGCGATCCTGCACCGCCGGAGCTTTCCACCC CGCG 3' (Seq. ID No. 11)

All Molecular Beacon sequences quoted in this specification have a 5' FAM (fluorophore) and a 3' methyl red (quencher).

Figure 5:
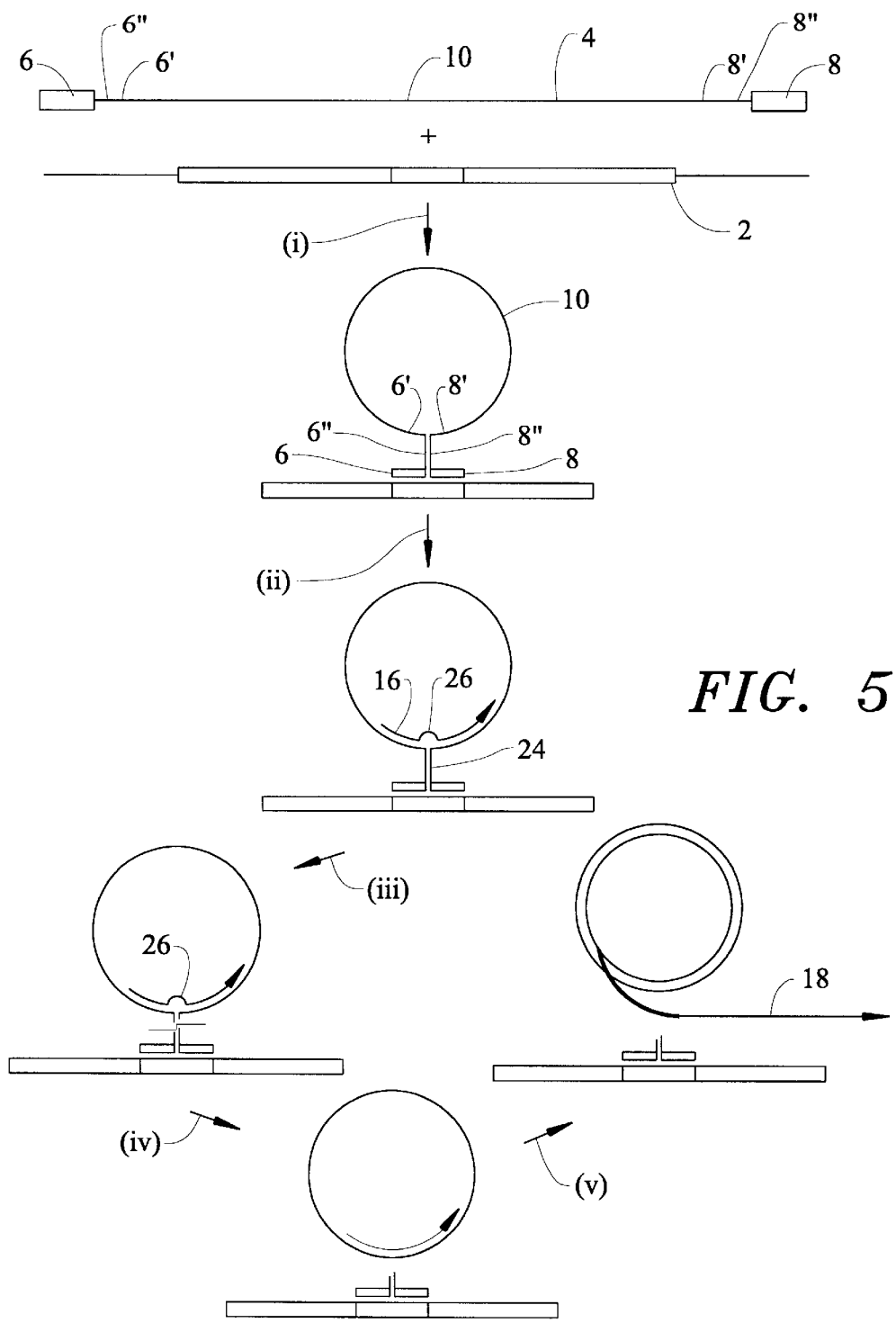

The Example is illustrated schematically in FIG. 5. Functionally equivalent integers are denoted by the same reference numerals as in FIGS. 1 and 2.

Referring to FIG. 5, steps (i) and (ii) are performed essentially as described previously. However, it should be noted that the first probe 4 comprises 5' and 3' self-complementary portions (6" and 8" respectively) which can anneal to each other, forming a stem 24, when stabilised by hybridisation to the target 2 of the 5' and 3' target-complementary portions 6 and 8 (step (i)). In addition, the second probe 16 comprises a region 26 which is complementary to the "top" part of the stem 24. Accordingly, when the double stranded stem 24 is cleaved by the action of a specific restriction endonuclease (step (iii)), the second probe 16 can become completely base paired with the first probe 4, which is released from the portions 6, 8 still hybridised to the target sequence 2. The first probe 4 thus has a double stranded region (where the second probe 16 is hybridised) with a single stranded nick, which can be joined by a ligase (step (iv)) to give a covalently closed circular molecule, which facilitates performance of rolling circle replication (step (v)). The newly synthesised nucleic acid 18 is a concatameric product which can readily be detected (e.g. by hybridisation to a molecular beacon oligonucleotide).

EXAMPLE 6

This example demonstrates a method in accordance with the second aspect of the invention in which the synthesis of a de novo nucleic acid strand is a result of the interaction of target nucleic acid (the cystic fibrosis transregulator (CFTR) gene), and hybridised probes to yield a de novo primer extended product.

6.1. Preparation of Oligonucleotides

First and second probes and all other oligonucleotides were synthesised by phosphoramidite chemistry using an Applied Biosystems 380A synthesiser, according to the manufacturer's instructions. All oligonucleotides were HPLC purified using standard techniques.

6.2. Preparation of Target DNA

DNA samples were obtained from a normal individual homozygous for the non-mutated CFTR gene. DNA was derived from blood lymphocytes in the following manner; 50 µl of whole blood was washed twice in TE (10 mMTris: 1 mM EDTA.pH8). The cells were then lysed in polymerase chain reaction (PCR) buffer containing 0.5% Tween 20 and Proteinase K (100 mg/ml). Cells were incubated at 55° C. for 1 hour followed by a heat inactivation step at 95° C. for 10 minutes.

The CFTR region of interest was than amplified by the polymerase chain reaction (PCR) procedure as outlined in EP200362). 10 µl of the DNA preparation was placed in a 0.2 ml microtube together with 5 µl 10×PCR buffer, dNTP mix (0.2 mM each), 1 unit AmpliTaq polymerase (Roche Molecular Systems Inc.) and 0.5 mM oligonucleotide amplification primers (CTFR oligos 1 and 2). Amplification was undertaken by 35 cycles in a thermal cycler (GeneAmp PCR System 2400—Roche Molecular Systems Inc.) comprising successive steps of 94° C. for 0.5 minutes, 55° C. for 0.5 minutes and 72° C. for 1 minute. The resulting 177 bp PCR product was purified by elution through a PCR preparation purification column (Qiagen Ltd.). Final PCR product concentration was made to 100 ng/ml.

6.3. Looping Out of Target Amplification

Figure 6:
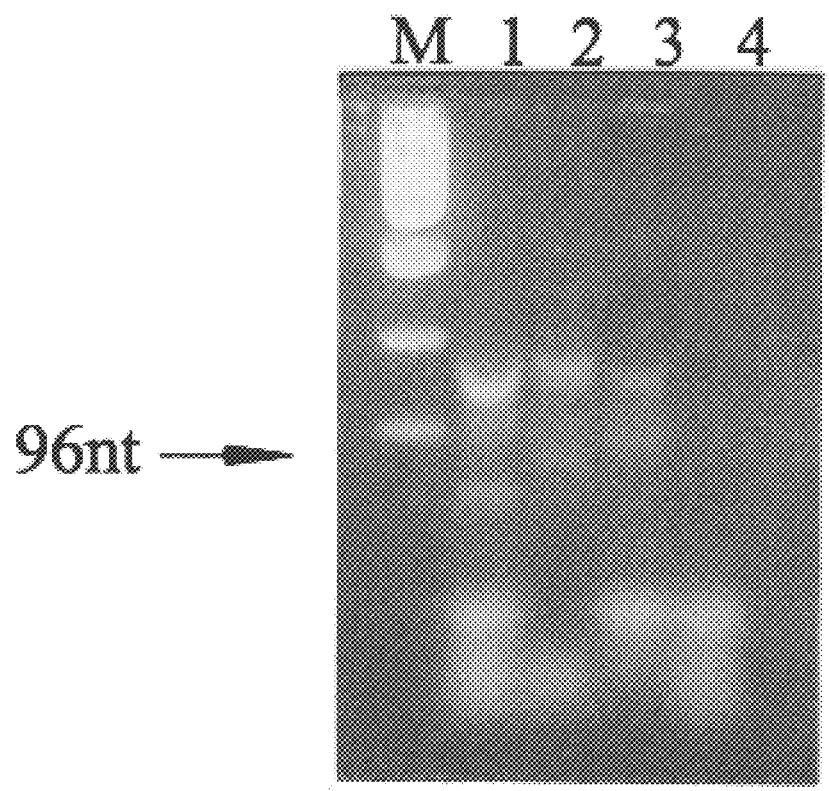
FIG. 6 is a photograph showing agarose gel electrophoresis detection of nucleic acid produced in performing the method of the second aspect of the invention.

Hybridisation reactions comprising mixtures of DNA including target DNA, and first and second probes, together with controls comprising mixtures with and without template or first and second probes were prepared. For hybridisation reactions, 100 ng of target CFTR DNA was mixed with 100 ng of first probe and 100 ng probe in a solution containing 0.2 mM dNTP mix, 2.5 ul 10×polymerase buffer (Boehringer Mannheim Gmbh) 1 unit Taq polymerase and distilled water to 25 ul. The mixture was heated to 94° C. for 0.5 minutes to denature the target nucleic acid, and primers annealed and extended at 45° C. for 1 minute. This procedure was repeated 20 times using a GeneAmp PCR System 2400—(Roche Molecular Systems Inc.). An aliquot (15 µl) of the resulting product was denatured at 94° C. for 1 minute prior to electrophoresis through a 3.5% Metaphor (FMC) agarose gel to observe and identify the primer extended product. The results of the agarose gel electrophoresis are shown in FIG. 6.

First Probe

5' TATTCATCATAGGAAACACCCTCCAGTTCTC CCATAATCAp 3' (Seq. ID No. 12)

Second Probe

5' CCCTCTGAAGGAAAGATGATATT 3' (Seq. ID No. 13)

CFTR Oligonucleotide 1

5' CACTTCTAATGATGATTATGG 3' (Seq. ID No. 14)

CFTR Oligonucleotide 2

5' GGCATGCTTTGATGACGCTTCTG 3' (Seq. ID No. 15)

Referring to FIG. 6, the figure shows gel electrophoresis analysis of the results of the primer extension reaction performed in accordance with the invention. The lane on the left labelled MA comprises molecular weight markers. The other lanes comprise the results of reactions as follows:

lane 1—4 μg/ml 177 bp CFTR PCR fragment (target sequence)÷first and second probes;

lane 2—control, as lane 1 but without first probe;

lane 3—control, as lane 1 but without second probe;

lane 4—control, as lane 1 but without target sequence.

It is apparent that only in lane 1 is the expected 96 bp nucleotide extension product obtained. No extension product is obtained in any of the control reactions.

EXAMPLE 7

Figure 7:
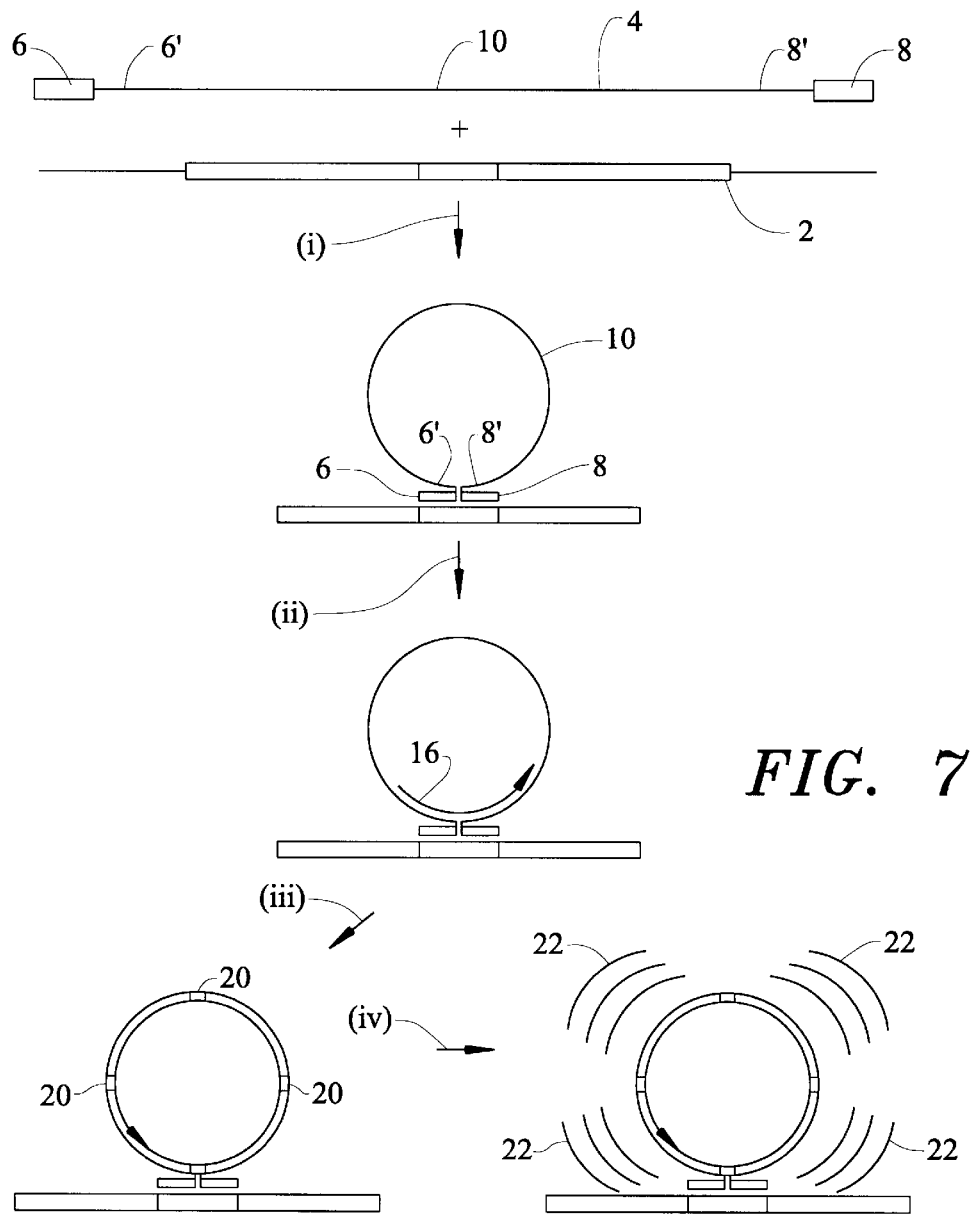
Figure 8:
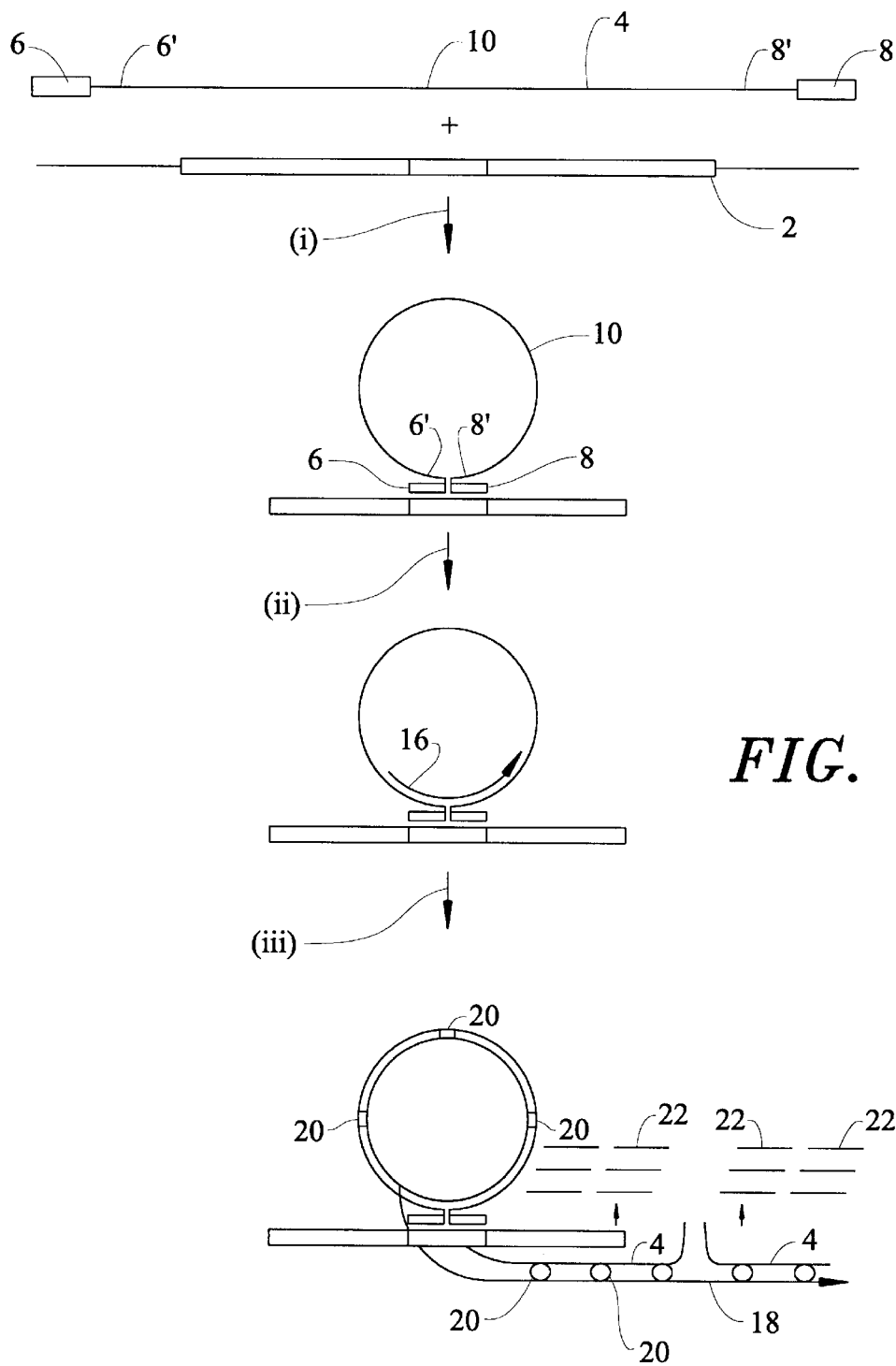

It will be evident to those skilled in the art that the above examples should not be deemed limiting and that sequences could be modified such that the loop contains sequences to a plurality of T7 or Sp6 RNA polymerase promoters. Upon primer extension of the second probe a plurality of active RNA polymerase promoters 20 is produced (FIG. 7, reference numerals as previously). It will also be obvious from the above examples that loop sequences containing a plurality of RNA polymerase promoter sequences 20 when copied on a concatameric molecule 18 via rollina circle amplification will become active when excess of the first probe 4 (loop sequence oligonucleotide) anneals to it. Therefore, in the presence of a specific RNA polymerase, multiple copies 22 of RNA molecules will be transcribed (FIG. 8, refernce numerals as previously).

What is claimed is:

1. A method of detecting the presence of a nucleic acid target sequence of interest in a sample, comprising the steps of:
   (a) reacting the sample containing the target sequence of interest with a first nucleic acid probe, so as to cause hybridisation between complementary portions of the target and the probe, wherein the probe comprises 5' and 3' portions complementary to respective portions of the target sequence which are adjacent or within 10 nucleotides of each other and an intervening non-complementary portion which does not become hybridised to the target, thereby creating a loop region looped out from a complex formed between the first probe and the target, such that non-contiguous portions of the first probe are brought into close proximity;
   (b) hybridising a second nucleic acid probe to non-contiguous looped out portions of the first probe,
   (c) initiating nucleic acid synthesis, using the first probe as template, in a manner dependent upon hybridisation of the second probe to the first probe; and
   (d) detecting the newly synthesised nucleic acid from step (c) above.

2. A method according to claim 1, wherein the second probe is extended by a polymerase using the first probe as a template.

3. A method according to claim 2, wherein the first probe comprises self-complementary sequences which become annealed when the 5' and 3' target-complementary portions are hybridised to the target sequence, said annealed self-complementary sequences forming a double stranded stem comprising a cleavage site.

4. A method according to claim 3, wherein the cleavage site is recognised by a restriction endonuclease.

5. A method according to claim 4, wherein the second probe comprises a sequence which is complementary to the sequence of the stem when the stem is cleaved at the cleavage site.

6. A method according to claim 3 wherein, following cleavage of the stem, the free ends of the stem are joined by a ligation step.

7. A method according to claim 1, wherein the first probe comprises one strand of one or more RNA promoters, and wherein the second probe comprises the complementary strand, such that hybridisation of the second probe to the first probe results in the formation of one or more active, double stranded RNA promoters which can initiate RNA synthesis in the presence of an RNA polymerase recognising the RNA promoter.

8. A method according to claim 1, wherein the first probe comprises one strand of one or more RNA promoters, and wherein extension of the second probe results in the synthesis of the complementary strand thereby forming one or more active, double stranded RNA promoters which can initiate RNA synthesis in the presence of an RNA polymerase recognising the RNA promoter.

9. A method according to claim 8, wherein a number of identical RNA promoters is formed, each of which is recognised by a single RNA polymerase.

10. A method according to claim 9, wherein the RNA promoter is recognised by T7 or Sp6 RNA polymerases.

11. A method of detecting the presence of a nucleic acid target sequence of interest in a sample, comprising the steps of:
    (a) reacting the sample containing the target sequence of interest with a first nucleic acid probe, so as to cause hybridisation between complementary portions of the target and the probe, wherein the target comprises 5' and 3' portions complementary to respective portions of the probe sequence which are adjacent or within 10 nucleotides of each other and an intervening non-complementary portion which does not become hybridised to the probe, thereby creating a loop region looped out from a complex formed between the first probe and the target, such that non-contiguous portions of the target are brought into close proximity;
    (b) hybridising a second nucleic acid probe to non-contiguous looped out portions of the target,
    (c) initiating nucleic acid synthesis, using the target as template, in a manner dependent upon hybridisation of the second probe to the target; and
    (d) detecting the newly synthesised nucleic acid from step (c) above.

12. A method according to claim 11, wherein the second probe is extended by a polymerase using the target as a template.

13. A method according to claim 12, wherein the target comprises one strand of one or more RNA promoters, and wherein the second probe comprises the complementary strand, such that hybridisation of the second probe to the target results in the formation of one or more active, double stranded RNA promoters which can initiate RNA synthesis in the presence of an RNA polymerase recognising the RNA promoter.

14. A method according to claim 13, wherein the target comprises one strand of one or more RNA promoters, and wherein extension of the second probe results in the synthesis of the complementary strand thereby forming one or more active, double stranded RNA promoters which can initiate RNA synthesis in the presence of an RNA polymerase recognising the RNA promoter.

15. A method according to claim 14, wherein a number of identical RNA promoters is formed, each of which is recognised by a single RNA polymerase.

16. A method according to claim 15, wherein the RNA promoter is recognised by T7 or Sp6 RNA polymerases.

17. A method according to claim 11, wherein the 3' end of the first probe and/or the target is blocked to prevent extension by a polymerase.

18. A method according to claim 11, wherein the second probe is extended by rolling circle replication.

19. A method according to claim 11, comprising the use of a strand displacement factor.

20. A method according to claim 11, wherein the newly-synthesised nucleic acid incorporates a labelling reagent.

21. A method according to claim 20, wherein the labelling reagent is a labelled nucleotide or nucleotide analogue.

22. A method according to claim 21, wherein the newly synthesised nucleic acid is detected by hybridisation to a molecular beacon sequence.

23. A kit for performing the method of claim 1, the kit comprising a first nucleic acid probe molecule for hybridisation to the target sequence of interest, a second nucleic acid probe molecule for hybridisation to non-contiguous looped out portions of the first probe molecule which are brought into close proximity upon hybridisation of the first probe to the target.

24. A kit for performing the method of claim 11, the kit comprising a first nucleic acid probe molecule for hybridisation to the target sequence of interest, a second nucleic acid probe molecule for hybridisation to non-contiguous looped out portions of the target which are brought into close proximity upon hybridisation of the first probe to the target.

25. A kit according to claim 24, further comprising at least one member from the group consisting of a DNA polymerase; an RNA polymerase; nucleotides (ribonucleotides or deoxyribonucleotides) for synthesis of nucleic acid; detection reagents; enzyme cofactors; strand displacement factors; and reaction buffers.

26. A method according to claim 1 wherein the probe comprises 5' and 3' portions complementary to respective portions of the target sequence which are adjacent or within 5 nucleotides of each other.

27. A method according to claim 11 wherein the target comprises 5' and 3' portions complementary to respective portions of the probe sequence which are adjacent or within 5 nucleotides of each other.

28. A kit according to claim 25 wherein the detection agents are labeled nucleotides or nucleotide analogues or molecular beacon sequences.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (xi) SEQUENCE DESCRIPTION: SEQ ID NO: 1:

TTTCTCCTGG CTCAGTTTAC TAGTGCCATT TGTTCAGTGG TTCGCAGGGC TTTCCCCCAC     60

TGTTTGGCTT T     71

(2) INFORMATION FOR SEQ ID NO: 2:

(i) SEQUENCE CHARACTERISTICS:
      (A) LENGTH: 102 base pairs
      (B) TYPE: nucleic acid
      (C) STRANDEDNESS: single
      (D) TOPOLOGY: linear (xi) SEQUENCE DESCRIPTION: SEQ ID NO: 2:

GGGAAAGCCC TGCGAACCAC TCGTGGAATG TTGCCCACAC CTAGTGCCCA CCGTGGAATG     60

TTGCCAACAC CTAGTGCCCA CGAACAAATG GCACTAGTAA AC     102

(2) INFORMATION FOR SEQ ID NO: 3:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO: 3:

CCACGGTGGG CACTA     15

(2) INFORMATION FOR SEQ ID NO: 4:

(i) SEQUENCE CHARACTERISTICS:
      (A) LENGTH: 70 base pairs
      (B) TYPE: nucleic acid
      (C) STRANDEDNESS: single
      (D) TOPOLOGY: linear (xi) SEQUENCE DESCRIPTION: SEQ ID NO: 4:

TCCCTTCAGA CGGCATTGTC AAGAATTTTA TTAAAAACAG GATTCCCATC ATGAACACCC     60

```
(2) INFORMATION FOR SEQ ID NO: 5:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (xi) SEQUENCE DESCRIPTION: SEQ ID NO: 5:

GGGCGGGGGT GTTCATGATG TTAATTTCAT CCTGCACCGC CGGAGCTTTC CACCCATCCT      60

GCACCGCCGG AGCTTTCCAC CCTCTCCCTA TAGTGAGTCG TAGGAATCCT GTTTTTAATA     120

AAATTC                                                                126

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 6:

GAAATTAATA CGACTCACTA TA                                               22

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 7:

CGCGATCCTG CACCGCCGGA GCTTTCCACC CCGCG                                 35

(2) INFORMATION FOR SEQ ID NO: 8:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO: 8:

GCGTCGTTTC CGCGTCGCTG GCCCCTGGGA GGCGTTCTTC GTGTGTCCCC GGGGACCCGC      60

GCTGCCGTCG                                                             70

(2) INFORMATION FOR SEQ ID NO: 9:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO: 9:

CCCCGGGGAC ACACGAAGAA AGGCCTCCCA CCTTTCGAGG CCGCCACGTC CTACCCACCT      60

TTCGAGGCCG CCACGTCCTA CCCACCTTTC GAGGCCGCCA CGTCCTTGAA GGCCTCGCCT     120

CCCAGGGGCC AGCGA                                                      135

(2) INFORMATION FOR SEQ ID NO: 10:
```

(preceding line: CCGCCCTCCT 70)

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

GGTGGGAGGC CTTCAAGGAC GTGG                                              24

(2) INFORMATION FOR SEQ ID NO: 11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 11:

CGCGATCCTG CACCGCCGGA GCTTTCCACC CCGCG                                   35

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 12:

TATTCATCAT AGGAAACACC CTCCAGTTCT CCCATAATCA                              40

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 13:

CCCTCTGAAG GAAAGATGAT ATT                                               23

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

CACTTCTAAT GATGATTATG G                                                 21

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

GGCATGCTTT GATGACGCTT CTG                                               23
```